(12) United States Patent
Kato

(10) Patent No.: US 7,087,311 B2
(45) Date of Patent: Aug. 8, 2006

(54) POLYMER COMPOUND, PRECURSOR FOR THE SAME AND THIN FILM-FORMING METHOD USING THE SAME POLYMER PRECURSOR

(75) Inventor: Takashi Kato, Yokohama (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 11/207,463

(22) Filed: Aug. 18, 2005

(65) Prior Publication Data

US 2006/0019109 A1    Jan. 26, 2006

Related U.S. Application Data

(62) Division of application No. 10/283,481, filed on Oct. 29, 2002, now Pat. No. 6,949,618.

(30) Foreign Application Priority Data

Dec. 26, 2001  (JP) ............. 2001-393985
Mar. 22, 2002  (JP) ............. 2002-081230

(51) Int. Cl.
  *B32B 27/00*   (2006.01)
  *C08G 69/28*   (2006.01)
(52) U.S. Cl. ............. 428/473.5; 428/411.1; 428/457; 428/458; 528/170; 528/353
(58) Field of Classification Search ............. 428/473.5, 428/411.1, 457–458; 528/170, 353
See application file for complete search history.

(56) References Cited

U.S. PATENT DOCUMENTS

| | | | | |
|---|---|---|---|---|
| 4,543,295 A | * | 9/1985 | St. Clair et al. ............ | 428/458 |
| 5,338,826 A | * | 8/1994 | St. Clair et al. ............ | 428/353 |
| 6,472,080 B1 | * | 10/2002 | Inagaki et al. ............. | 428/450 |
| 6,949,618 B1 | * | 9/2005 | Kato ......................... | 528/170 |
| 2006/0019109 A1 | * | 1/2006 | Kato ......................... | 428/473.5 |

* cited by examiner

*Primary Examiner*—P. Hampton Hightower
(74) *Attorney, Agent, or Firm*—J.C. Patents

(57) ABSTRACT

Provided are polyimide and a thin film thereof which have a three-dimensional structure and therefore are excellent in a mechanical strength and a heat resistance as compared with those of conventional linear polyimide. The polyimide is obtained from a salt of multifunctional amine represented by Formula (1):

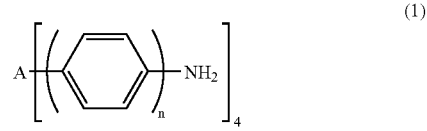

(1)

(wherein A represents a tetravalent organic group, and n represents an integer of 0 to 3) and tetracarboxylic diester represented by Formula (2):

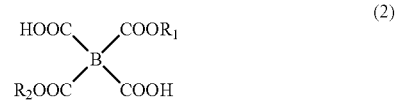

(2)

(wherein B represents a tetravalent organic group having 1 to 20 carbon atoms, and $R_1$ and $R_2$ each represent independently an alkyl group having 1 to 5 carbon atoms).

6 Claims, 3 Drawing Sheets

POLYMER COMPOUND, PRECURSOR FOR THE SAME AND THIN FILM-FORMING METHOD USING THE SAME POLYMER PRECURSOR

CROSS-REFERENCE TO RELATED APPLICATION

This application is divisional application of, and claims the priority benefit of, U.S. application Ser. No. 10/283,481 filed on Oct. 29, 2002 now U.S. Pat. No. 6,949,618, which claims the priority benefit of Japan applications serial no. 2001-393985, filed Dec. 26, 2001, and 2002-081230, filed Mar. 22, 2002.

BACKGROUND OF THE INVENTION

1. Field of the Invention

The present invention relates to a novel polyimide having a rigid three-dimensional structure. Further, it relates to a novel polyimide precursor making it possible to produce the polyimide of the present invention and the thin film thereof by a simple method which is not likely to cause gelation, and a solution thereof.

The polyimide thin film of the present invention is used as a layer insulating film for integrated circuits (LSI) in microelectronics and an aligning film for liquid crystal displays.

2. Description of the Related Art

In recent years, fineness and high speed of LSI using copper wires are desired. A dielectric constant of a layer insulating film has to be reduced in order to meet them, and development thereof is actively carried out at present, which results in successive publication of the new materials. In the greater part thereof, a dielectric constant thereof is reduced by making use of a dielectric constant (1.0) of the air to introduce a hole into a material. However, simple dispersion of holes in the structure has brought about the problem that an increase in the hole rate results in a reduction in the mechanical strength.

In order to solve this problem, it is tried in several cases to allow a mechanical strength and a low dielectric constant to stand together by controlling a size of the holes and a form of the material at a nanometer level. For example, disclosed in Shingaku Technical Report, SDM2000-194 (2001) is the proposal that a limiting low dielectric constant and a high strength can be achieved by regularly forming nanoholes of a molecular level between structural units of a three-dimensional organic polymer having a pseudo-diamond structure.

Further, polyimide comprising tetraminoadamantane and benzenetetracarboxylic acid is disclosed in Japanese Patent Laid-Open No. 332543/2001, but polyimides having the other structures are not disclosed at all.

The most general method for producing a polyimide thin film is a method in which diamine and tetracarboxylic dianhydride are subjected to polycondensation reaction in a solvent to prepare a polyamic acid solution and in which it is then dehydrated by heating or a chemical method to form an imide ring. However, when the above method is applied to multifunctional amino compounds higher than triamine, a three-dimensional cross-linking structure is formed by polyaddition reaction, and a solvent is taken thereinto to cause gelation. A gel has the defects that it is an insoluble swollen substance and uneasy to handle and that it is very difficult to form a molded matter such as a thin film.

A vapor deposition polymerization method is introduced as a polyimide synthetic method using no solvent in Salon et al., Journal of Vacuum Science and Technology 1986, vol. A4, p. 369, but an expensive vapor deposition apparatus is needed for this vapor deposition method, and it is not necessarily a simple and industrial method.

SUMMARY OF THE INVENTION

An object of the present invention is to provide a precursor for readily producing polyimide without causing gelation in the middle of synthesis even if using a multifunctional amino compound as a monomer.

Further, it is to provide a novel polyimide having a three-dimensional structure using a solution of such precursor and a thin film thereof.

The present inventors have repeated intensive researches from a viewpoint of preventing gelation by carrying out polymerization on a non-solvent condition. As a result thereof, they have found that a novel polyimide having a three-dimensional structure can readily be synthesized without causing gelation by using diester of tetracarboxylic acid in place of tetracarboxylic dianhydride having a high reactivity, that is, using a salt of multifunctional amine and diester of tetracarboxylic acid as a precursor, and thus they have come to complete the present invention.

That is, the polyimide of the present invention is characterized by applying a multifunctional amine-tetracarboxylic acid diester salt solution which is a precursor thereof on a substrate, evaporating the solvent at a relatively low temperature and then further subjecting the thin film precursor remaining on the substrate to heat treatment to thereby turn it into imide by dehydration and dealcohol reactions.

The present invention comprises the following structures.

(1) A salt of a multifunctional amine represented by Formula (1):

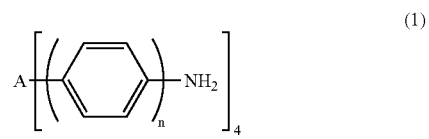

(wherein A represents a tetravalent organic group, and n represents an integer of 0 to 3) and tetracarboxylic diester represented by Formula (2):

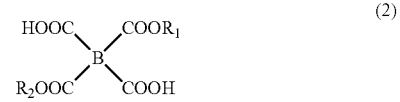

(wherein B represents a tetravalent organic group having 1 to 20 carbon atoms, and $R_1$ and $R_2$ each represent independently an alkyl group having 1 to 5 carbon atoms).

(2) The salt of multifunctional amine and tetracarboxylic diester as described in the item (1), wherein A in Formula (1) is an adamantane skeleton.

(3) The salt of multifunctional amine and tetracarboxylic diester as described in the item (1), wherein A in Formula (1) is a diamantane skeleton.

(4) A precursor of polyimide characterized by using the salt as described in any of the items (1) to (3).

(5) A polyimide precursor solution, wherein the polyimide precursor as described in the above item (4) is dissolved in an organic solvent.

(6) A polyimide thin film obtained by applying the polyimide precursor solution as described in the item (5) on a substrate, evaporating the solvent to form a film and then heating and baking it.

(7) The polyimide thin film as described in the item (6) comprising polyimide having a three-dimensional structure represented by Formula (3):

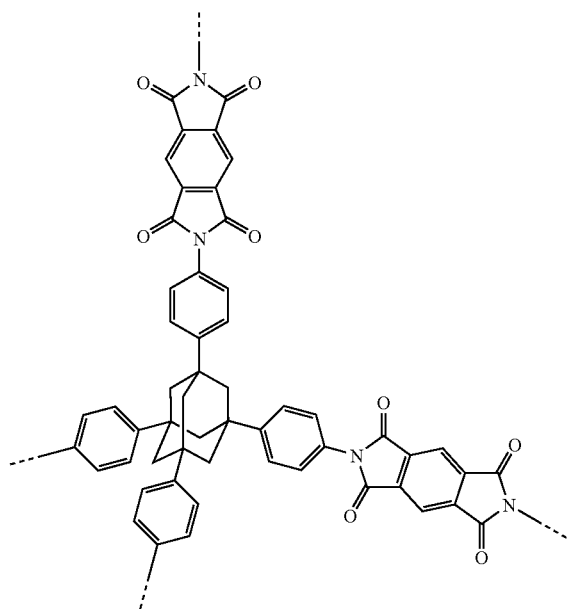

(3)

(8) A layer insulating film using the polyimide thin film as described in any of the items (6) to (7).

(9) A polyimide represented by Formula (4):

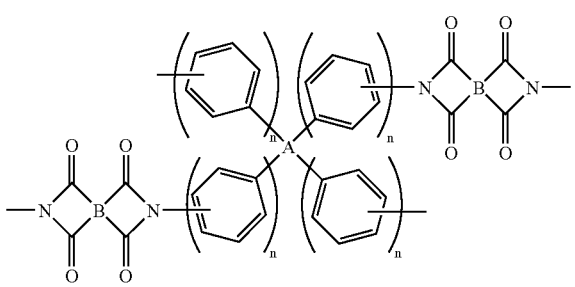

(4)

(wherein A represents a tetravalent organic group; B represents a tetravalent organic group having 1 to 20 carbon atoms; and n represents an integer of 0 to 3).

(10) The polyimide as described in the item (9), wherein A in Formula (4) is an adamantane skeleton.

(11) The polyimide as described in the item (9), wherein A in Formula (4) is a diamantane skeleton.

(12) The polyimide as described in any of the items (9) to (11), wherein B in Formula (4) is a benzene ring or a biphenyl ring.

(13) A polyimide having the three-dimensional structure represented by Formula (3) as described in the item (7).

(14) A polyimide represented by Formula (5):

(5)

-continued

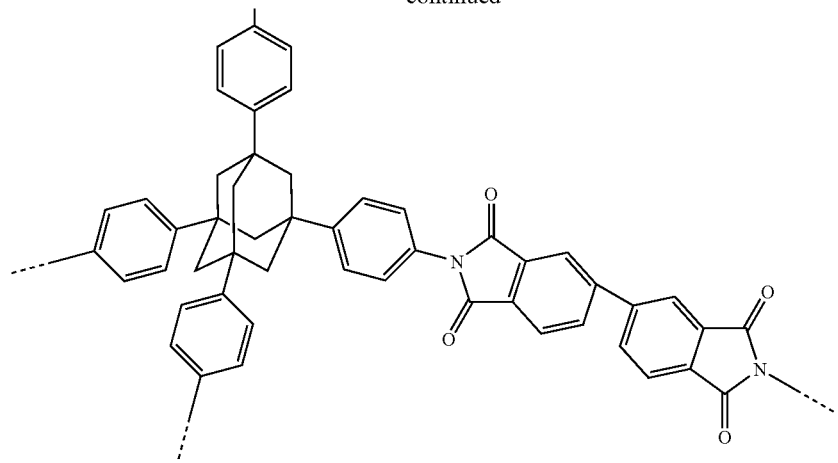

(15) An electric fixing apparatus characterized by using the polyimide as described in any of the items (9) to (14) as a layer insulating film.

DETAILED DESCRIPTION OF THE PREFERED EMBODIMENTS

Figure 1:
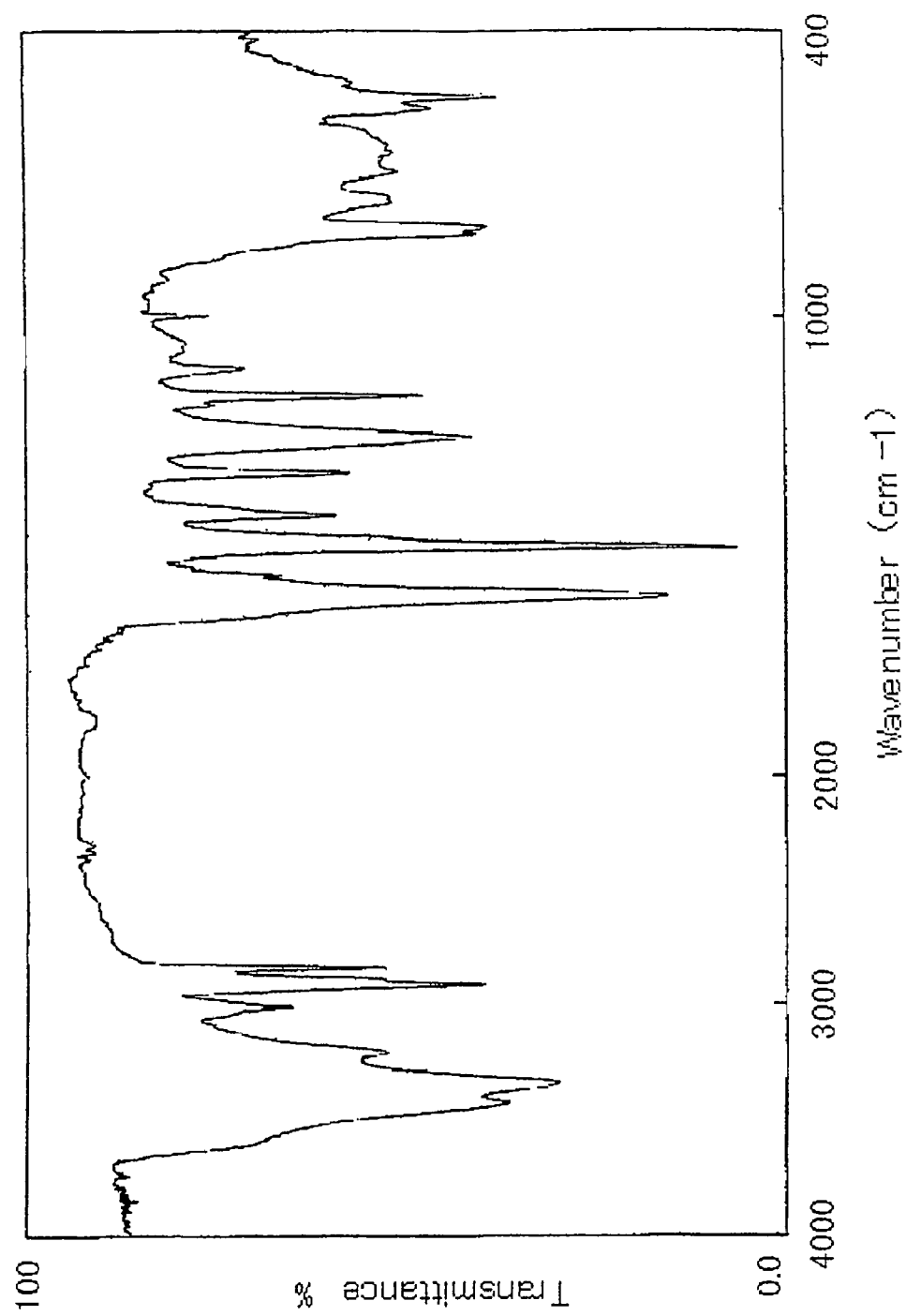
FIG. 1 is an IR spectrum of 1,3,5,7-tetrakis(4-aminophenyl)adamantane synthesized in [1] of Example 1.

The polyimide of the present invention is obtained from a solution of a salt of multifunctional amine and tetracarboxylic acid diester which is a precursor of the polyimide of the present invention. For example, a multifunctional amine and tetracarboxylic acid diester may be blended in an organic solvent. A reaction example thereof shall be shown below:

(1) + (2) ⟶

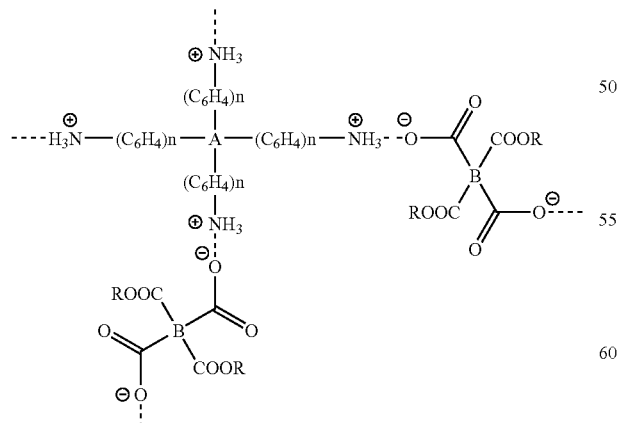

A bond of this salt is weaker than a covalent bond of polyamic acid, and therefore a strong cross-linking network structure can not be formed in a solution. Accordingly, the solution is not likely at all to be gelatinized.

The polyimide precursor solution thus obtained is applied in the form of a vanish on a substrate such as a glass plate, a copper plate, an aluminum plate or a silicone wafer, and then the substrate is heated at a temperature lower than a boiling point of the solvent for short time to evaporate the solvent. Thereafter, the filmy precursor remaining on the substrate is heated and baked at 200 to 450° C., whereby an amide bond is formed by dehydration reaction from the salt. When using multifunctional amine, gelation is ought to take place at this stage, but the solvent which is indispensable for gelation has already been almost evaporated, so that gelation is no longer caused. A reaction example thereof shall be shown below:

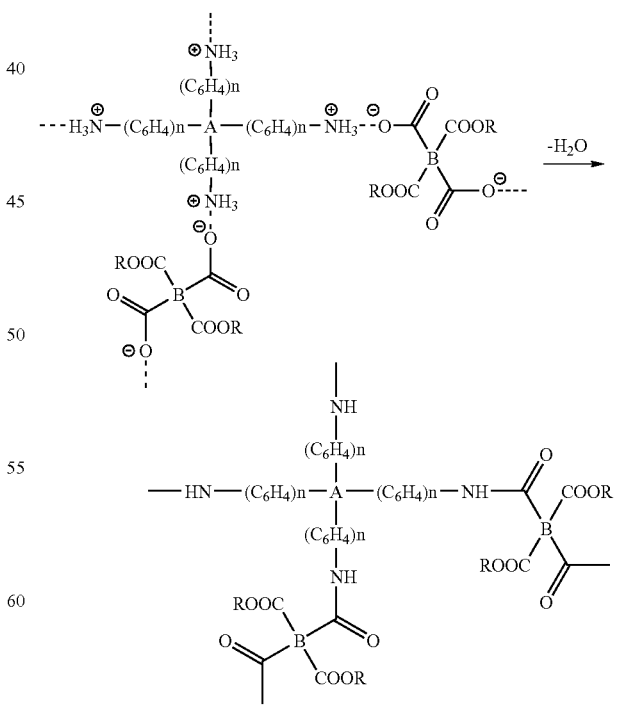

When heating is further continued, an intramolecular dealcohol reaction takes place between the amide bond and an adjacent carboxylic acid ester (alkoxycarbonyl group), and finally an imide ring is formed. A reaction example thereof shall be shown below:

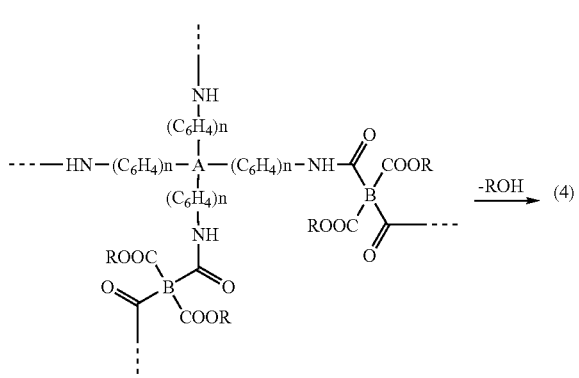

In the polyimide and the precursor thereof according to the present invention, the compound used as the multifunctional amino compound is a tetraamine derivative represented by Formula (1). A in the formula shall not specifically be restricted as long as it is a tetravalent organic group.

A in the tetraamine derivative represented by Formula (1) is the same as A in the polyimide represented by Formula (4) which is derived from this. However, in the case of the mixture, the composition, ratio thereof itself is not necessarily the same because of a difference in the reactivity.

The organic group which can be used for the polyimide and the precursor thereof according to the present invention is not specifically restricted in elements and is a part of a structure constituting the organic compound, and the specific structure has a skeleton structure shown below:

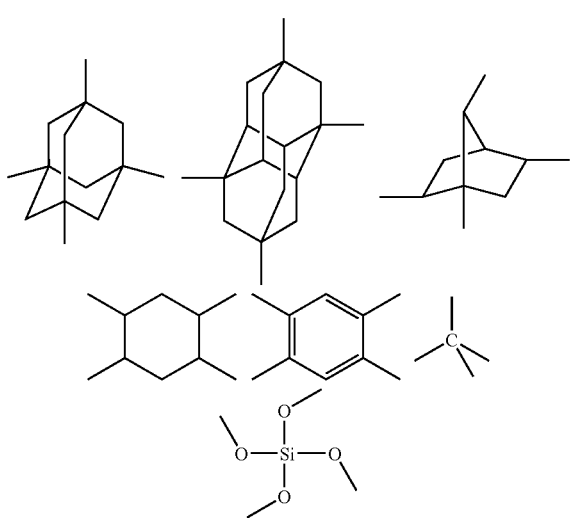

Among them, the organic group which can be used for the polyimide and the precursor thereof according to the present invention is preferably the following structures which can have a regular tetrahedron, more preferably an adamantane skeleton, a diamantane skeleton and a quaternary carbon atom.

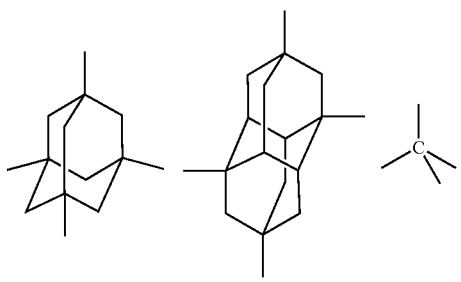

In the polyimide precursor according to the present invention and the solution thereof, the tetracarboxylic diester represented by Formula (2) can readily be synthesized by a conventional organic synthetic method. That is, most preferred is a method which is widely used at present in synthesis of polyimide, in which tetracarboxylic dianhydride is subjected to ring opening with excess alcohol. In this case, it is not problematic at all to use suitable solvents other than alcohol and add a base component such as pyridine as an acylation catalyst. Also, two kinds of the intended structure are present in a certain case depending on the mode of the reaction, and they may be used in the form of a mixture without isolating. Further, mixed tetracarboxylic diester obtained by reaction using two or more kinds of alcohols may be used. Allowed to be contained therein are triester and tetraester which are obtained by further esterification of the resulting diester by excess alcohol. In this case, tetraester neither forms a salt nor inhibits salt formation of other carboxylic acids, and therefore it may be contained.

The formula of this reaction and the specific example thereof using pyromellitic anhydride are shown below:

Formula

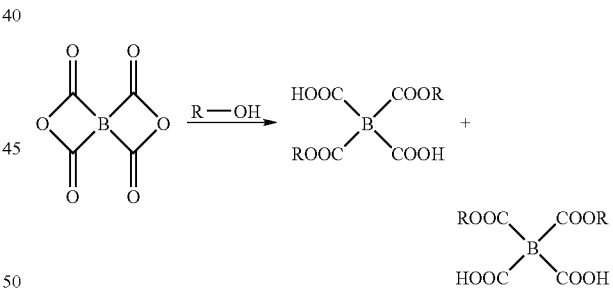

Specific Example

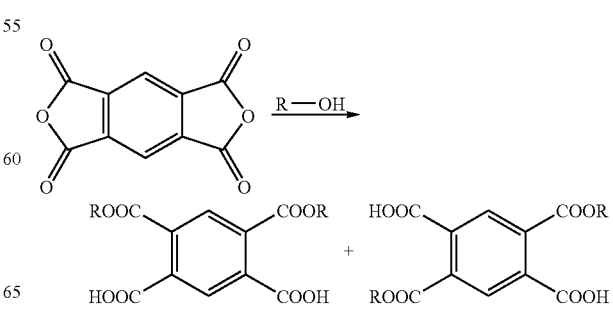

These tetracarboxylic dianhydrides which are raw materials for diesters can be considered according to the compound represented by Formula (2). That is, B in Formula (2) shall not specifically be restricted as long as it is a tetravalent organic group having 1 to 20 carbon atoms. Specific examples thereof include pyromellitic dianhydride, 3,3'4,4'-biphenyltetracarboxylic dianhydride, 2,2'3,3'-biphenyltetracarboxylic dianhydride, 2,3,3',4'-biphenyltetracarboxylic dianhydride, 3,3'4,4'-benzophenonetetracarboxylic dianhydride, 2,3,3',4'-benzophenonetetracarboxylic dianhydride, 2,3,3',4'-benzophenonetetracarboxylic dianhydride, 2,2'3,3'-benzophenonetetracarboxylic dianhydride, bis(3,4-dicarboxyphenyl)ether dianhydride, bis(3,4-dicarboxyphenyl)sulfone dianhydride, 1,2,5,6-naphthalenetetracarboxylic dianhydride, 2,3,6,7-naphthalenetetracarboxylic dianhydride, bis(dicarboxyphenyl)methane dianhydride, cyclobutanetetracarboxylic dianhydride, cyclopentanetetracarboxylic dianhydride, cyclohexanetetracarboxylic dianhydride, dicyclohexanetetracarboxylic dianhydride, dicyclopentanetetracarboxylic dianhydride, bis(dicarboxycyclohexl)ether dianhydride, bis(dicarboxycyclohexl)sulfone dianhydride, bis(dicarboxycyclohexl)methane dianhydride and 4,4'-(hexafluoroisopropylidene)diphthalic dianhydride.

Among them, preferred are pyromellitic dianhydride, 3,3'4,4'-biphenyltetracarboxylic dianhydride, 3,3'4,4'-benzophenonetetracarboxylic dianhydride, bis(3,4-dicarboxyphenyl)ether dianhydride, cyclobutanetetracarboxylic dianhydride and 4,4'-(hexafluoroisopropylidene)diphthalic dianhydride. Those containing isomers are included in these compounds, and they may be isomer mixtures. Further, two or more kinds of the compounds may be used in combination.

B in polyimidetetracarboxylic dianhydride represented by Formula (2) is the same as B in the polyimide represented by Formula (4) which is derived from this. However, in the case of the mixture, the composition ratio thereof itself is not necessarily the same because of a difference in the reactivity.

For example, when tetracarboxylic dianhydride is pyromellitic dianhydride, B in Formula (2) and Formula (4) is a benzene ring. Further, when it is 3,3'4,4'-biphenyltetracarboxylic dianhydride, B in Formula (2) and Formula (4) is a biphenyl ring.

Further, when multifunctional amine having an adamantane skeleton and pyromellitic dianhydride are used as the raw materials, polyimide represented by Formula (3) is obtained, and when multifunctional amine having an adamantane skeleton and 3,3'4,4'-biphenyltetracarboxylic dianhydride are used as the raw materials, polyimide represented by Formula (5) is obtained.

In the polyimide according to the present invention, a solvent used in preparing a solution of the multifunctional amine-tetracarboxylic diester salt which is the precursor shall not specifically be restricted as long as it can dissolve the raw materials and the salt, but solvents having a markedly high boiling point are not suited. To be specific, preferred are N-methyl-2-pyrrolidone, formamide, N,N-dimethylformamide, N,N-dimethylacetamide, N,N-dimethylimidazolidinoe, dimethylsulfoxide, hexamethylphosphoric acid triamide, dioxane, tetrahydrofuran, sulfolane and γ-butyrolactone, and more preferred are N-methyl-2-pyrrolidone, N,N-dimethylformamide and N,N-dimethylacetamide. These solvents may be used alone or in a mixture of a plurality thereof.

In producing the polyimide according to the present invention, the multifunctional amine-tetracarboxylic diester salt which is the precursor can be used for producing a thin film in the form of a solution dissolved in the solvent used in preparing the solution. That is, the multifunctional amine-tetracarboxylic diester salt does not have to be particularly isolated and refined.

Further, the other solvents having a low surface tension may be used in combination, if necessary, for the purpose of improving the coating characteristic. To be specific, capable of being given are alkyl lactate, 3-methyl-3-methoxybutanol, tetralin, isophorone, ethylene glycol monoalkyl ethers (ethylene glycol monobutyl ether and the like), diethylene glycol monoalkyl ethers (diethylene glycol monoethyl ether and the like), ethylene glycol monoalkyl or phenyl acetate, triethylene glycol monoalkyl ether, propylene glycol monoalkyl ether (propylene glycol monobutyl ether and the like), dialkyl malonate (diethyl malonate and the like), cyclohexanone and cyclopentanone. These solvents are poor solvents in many cases while the foregoing solvents are good solvents. Accordingly, they are added preferably in such an amount that the dissolved components are not deposited.

A method usually used can be used as a method for applying the precursor solution dissolved in these solvents on a substrate on which a layer insulating film is formed. For example, a spinner method, a printing method, a dipping method and a dropping method can be used.

In heat treatment required for drying the solvent after applying this solution, the same method as methods used in conventional layer insulating films can be carried out. For example, an oven, a hot plate and an infrared furnace can be used. After applying the solution, the solvent is vaporized at a relatively low temperature, and then heat treatment is preferably carried out at a temperature of 200 to 450° C., preferably 300 to 400° C. In this case, heating is carried out more preferably on a condition of nitrogen atmosphere or reduced pressure. Heating time is varied depending on the substrate, and it is preferably 30 to 180 minutes, more preferably about 60 to 120 minutes.

EXAMPLES

The present invention shall be explained below in further details with reference to examples, but the present invention shall by no means be restricted by these examples.

The physical properties of the compounds obtained in the examples were measured by the following methods.

Infrared Absorption Spectrum (IR):

Measured at room temperature by a KBr method by means of model FT/IR-7000 manufactured by Nippon Bunko Co., Ltd. Proton NMR spectrum ($^1$H-NMR):

Measured at room temperature by means of EX-90A manufactured by Nippon Electron Co., Ltd. at 90 MHz using DMSO-$d_6$ as a solvent and tetramethylsilane as an internal standard substance.

Example 1

[1] Synthesis of 1,3,5,7-tetrakis(4-aminophenyl)adamantane 1,3,5,7-Tetrakis(4-aminophenyl)adamantane (compound 3) was synthesized by a method described in Laychart et al., Macromolecules, vol. 27, p. 7024 (1994), which was shown in a reaction equation described later.

Detailed explanations shall be given below by every step.
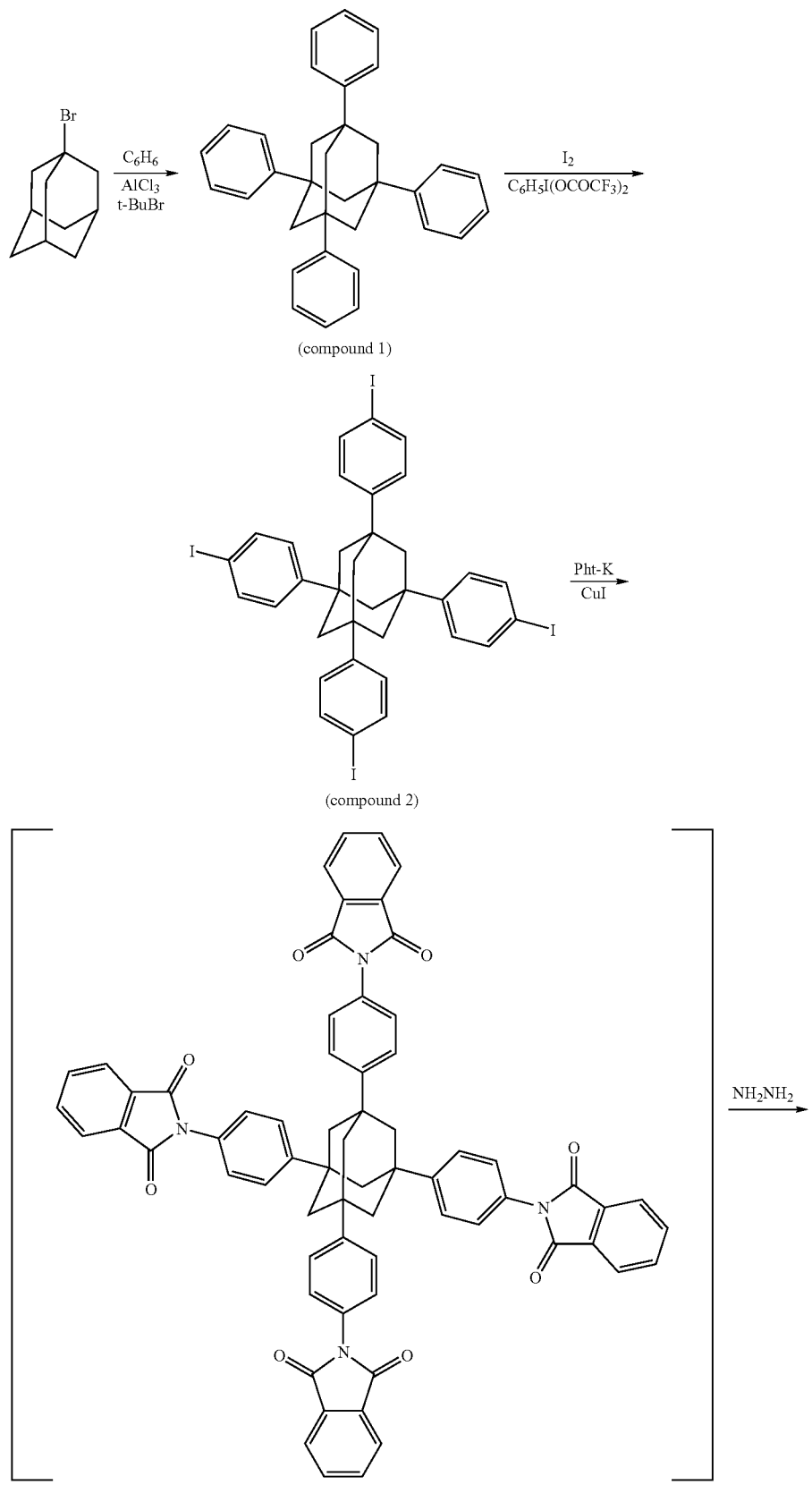

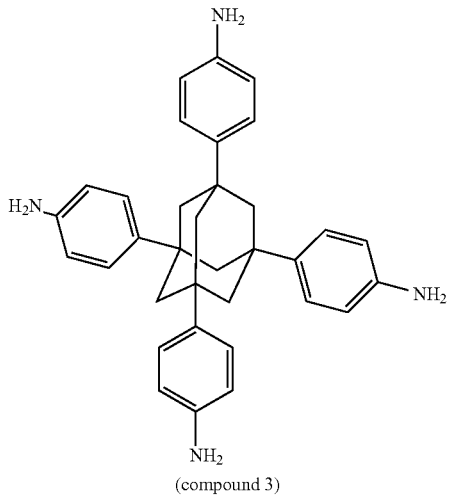

(compound 3)

[1]-(1) Synthesis of 1,3,5,7-tetraphenyladamantane (Compound 1)

A three neck flask of one liter equipped with a nitrogen-introducing tube, a cooling tube and a stirrer was charged with 30.0 g (0.14 mol) of 1-bromoadamantane and 38.2 g (0.28 mole) of t-butyl bromide, and they were dissolved in 300 ml of benzene and stirred at 0° C. Anhydrous aluminum chloride 1.6 g (0.012 mole) divided into four portions was added to this solution in the form of a solid. The reaction solution was stirred for one hour after returned to room temperature, and then it was heated and refluxed for further one hour.

After finishing the reaction, the reaction solution was poured into excess diluted hydrochloric acid cooled with ice and left standing for one hour. A deposited solid substance was filtered and dried under reduced pressure. This solid substance was put into a three neck flask of one liter equipped with a cooling tube and a stirrer and suspended in 500 ml of chloroform, and it was stirred for one hour under refluxing. The suspension was quickly filtered while it was hot to obtain 3.0 g (yield: 70%) of the intended compound of a white insoluble solid matter. This compound was used for a subsequent reaction without being refined any more.

[1]-(2) Synthesis of 1,3,5,7-tetrakis(4-iodophenyl)adamantane (Compound 2)

Put into a mortar were 120.0 g (0.045 mole) of the compound synthesized in [1]-(1) described above and 23.0 g (0.090 mole) of iodine, and they were sufficiently crushed and blended with a pestle. The resulting pink powder was put into an Erlenmeyer flask of 500 ml, and 200 ml of chloroform was added thereto, followed by stirring the solution at room temperature under nitrogen flow. Added thereto was 39.0 g (0.090 mole) of [bis(trifluoroacetoxy)iodo]benzene, and the solution was stirred for 4 hours.

The reaction solution was filtered, and the resulting solid matter was suspended in 300 ml of chloroform and stirred for one hour under refluxing. The solution was filtered while it was hot to remove the insoluble raw materials. The whole filtrates were put together and washed twice with a 5% sodium thiosulfate solution and twice with refined water. After the organic layer was dried on anhydrous magnesium sulfate, the desiccant was filtered off, and the solvent was distilled off under reduced pressure. A crude crystal thus obtained was recrystallized from chloroform to obtain 226.3 g (yield: 62%) of the intended compound of a colorless needle crystal.

[1]-(3) Synthesis of 1,3,5,7-tetrakis(4-aminophenyl)adamantane (compound 3)

A three neck flask of 300 ml equipped with a cooling tube, a stirrer and a mantle heater was charged with 5.0 g (5.30 mmole) of the compound synthesized in [1]-(2) described above, 3.9 g (21.2 mmole) of potassium phthalimide and 4.20 g (20.2 mmole) of copper iodide, and they were dissolved in 100 ml of N,N-dimethylacetamide (hereinafter referred to as DMAc) and refluxed for 12 hours under nitrogen flow by heating. After finishing the reaction, the solution temperature was returned to room temperature, and the solution was thrown into an excess 5 weight % sulfuric acid aqueous solution to filter a deposited solid matter. Further, the solid matter was sufficiently washed with dichloromethane, and the filtrate was extracted twice with dichloromethane. The organic layer was washed twice with refined water and dried on anhydrous magnesium sulfate. Then, the desiccant was filtered off, and the solvent was distilled off under reduced pressure. A yellow crude crystal thus obtained was recrystallized from a methanol/dichloromethane mixed=4/1 mixed solution to obtain 4.30 g (yield: 79%) of a tetraphthalimide compound of a white crystal.

Subsequently, a three neck flask of 300 ml equipped with a cooling tube and a stirrer was charged with 3.50 g (3.43 mmole) of the tetraphthalimide compound and 100 ml of ethanol, and the solution was stirred at room temperature under nitrogen flow. Added thereto was 10 g of hydrazine hydrate, and the solution was heated and refluxed for 4 hours. The reaction solution was thrown into excess water to filter a deposited solid matter. After drying the solid matter under reduced pressure, it was dissolved in excess hot chloroform, and the solution was quickly filtered while it was hot to remove insoluble phthalhydrazide. The filtrate was concentrated under reduced pressure, and the resulting solid matter was washed with methanol to obtain 1.50 g (yield: 87%) of 1,3,5,7-tetrakis(4-aminophenyl)adamantane (compound 3) of the intended compound.

IR and NMR spectra of this compound were consistent with the literature values. The IR spectrum is shown in FIG. 1.

A chemical shift of $^1$H-NMR was δ 1.83 (s, 12H), 4.80 (s, 8H), 6.53 (d, 8H), 7.04 to 7,19 (m, 8H).

[2] Production of Multifunctional amine-tetracarboxylic diester Salt Solution

A sample bottle was charged with 0.5007 g (1.0 mmol) of 1,3,5,7-tetrakis(4-aminophenyl)adamantane (in Formula (1), A=an adamantyl group, and n=1) obtained by synthesis in [1] described above, and it was dissolved in 10.1 g of DMAc at room temperature.

Added to this solution was 0.6205 g (2.0 mmol) of diethyl pyromellitate (in Formula (2), B=a benzene ring, and $R_1=R_2=$ethyl), and it was stirred at room temperature until it became a homogeneous solution. After stirred for about one hour, the solution was filtered through a membrane filter of 0.2 μm to obtain a brown polyimide precursor solution.

[3] Production of polyimide (Thin Film)

The polyimide precursor solution obtained in [2] described above was applied as a coating solution on a glass substrate by a spinner method and heated on a hot plate of 150° C. for one minute. The solvent was almost vaporized, and a brown filmy residue was obtained. Immediately, it was put in an oven and baked at 400° C. for one hour. A part of the resulting thin film was peeled off and measured for an IR spectrum by a KBr method to confirm absorptions showing formation of an imidocarbonyl group in the vicinities of 1780 cm$^{-1}$ and 1720 cm$^{-1}$, polypyromellitimide in the vicinities of 1375 cm$^{-1}$ and 720 cm$^{-1}$. The absorption showing formation of this polypyromellitimide was consistent with that described in Industrial Chemical Magazine, 69, 1069 (1966).

Figure 2:
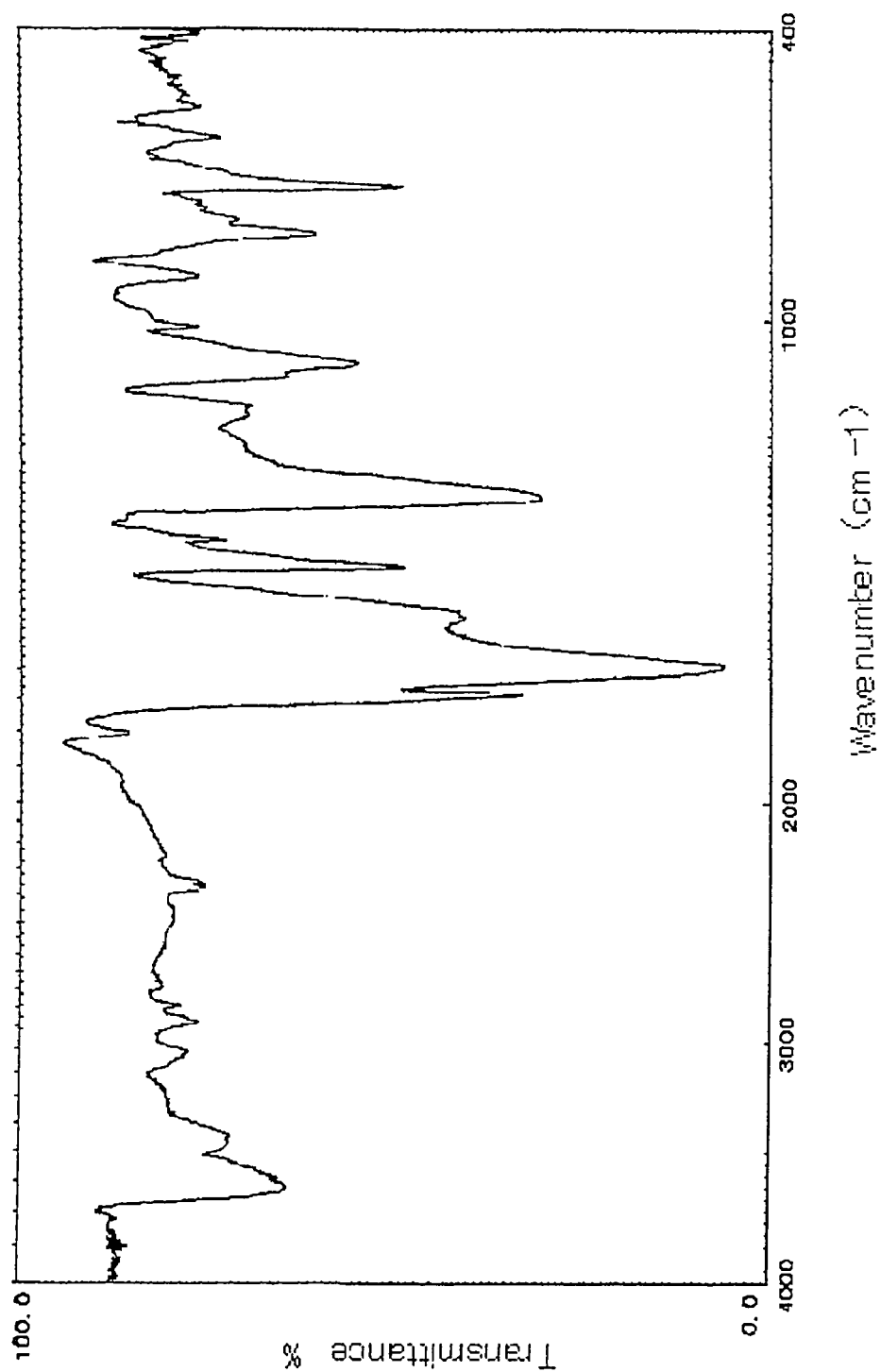
FIG. 2 is an IR spectrum of polyimide synthesized in Example 1.

This IR spectrum is shown in FIG. 2. It is apparent from this result that the polyimide of the present invention having a three-dimensional structure was formed without causing gelation during synthesis by using the polyimide precursor of the present invention and the solution thereof.

Example 2

A brown polyimide precursor solution was obtained according to Example 1, and then a thin film was formed, except that 0.7728 g (2.0 mmol) of diethyl 3,3',4,4'-biphenyltetracarboxylate (in Formula (2), B=a biphenylene group, and $R_1=R_2=$ethyl) was used as tetracarboxylic acid diester and that 11.5 g of DMAc was used.

Figure 3:
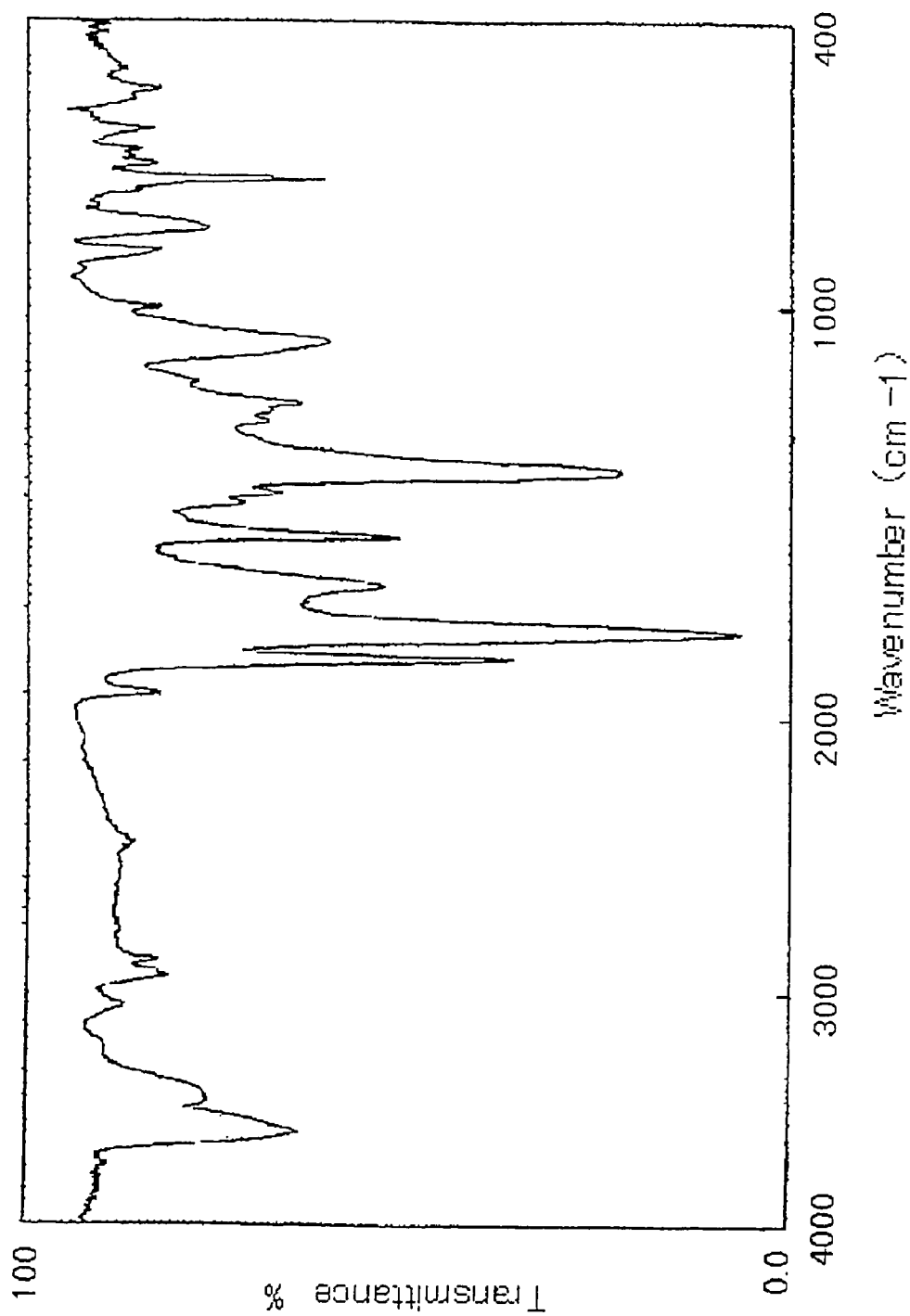
FIG. 3 is an IR spectrum of polyimide synthesized in Example 2.

This IR spectrum is shown in FIG. 3. It is apparent from this result that the polyimide of the present invention having a three-dimensional structure was formed without causing gelation during synthesis by using the polyimide precursor of the present invention and the solution thereof.

Comparative Example 1

A sample bottle was charged with 0.5007 g (1.0 mmol) of 1,3,5,7-tetrakis(4-aminophenyl)adamantane, and it was dissolved in 8.34 g of DMAc at room temperature. Pyromellitic dianhydride 0.4362 g (2.0 mmol) was added little by little to this solution in the form of a solid matter to find that a gelatinized insoluble matter was gradually deposited and that finally, the whole part of the reaction solution was covered with a swollen gel.

The resulting substance was a gel and therefore could not be coated.

EFFECTS OF THE INVENTION

The polyimide of the present invention and the thin film thereof have a three-dimensional structure and therefore are excellent in a mechanical strength and a heat resistance as compared with those of conventional linear polyimide, so that it is useful as a functional thin film such as a layer insulating film and a liquid crystal aligning film.

Further, the polyimide precursor of the present invention is not likely to cause gelation if a multifunctional amino compound is used, and it is so useful that polyimide having a three-dimensional structure and a thin film thereof can readily be produced.

Further, the polyimide of the present invention can be used for producing a thin film as it contains a solvent used in producing a solution of a multifunctional amine-tetracarboxylic diester salt which is the precursor. That is, the multifunctional amine-tetracarboxylic diester salt does not have to be isolated and refined, so that it is effective as well from an industrial point of view.

What is claimed is:

1. A polyimide thin film obtained by applying a polyimide precursor solution on a substrate, evaporating solvent to form a film and then heating and baking the film, wherein the polyimide precursor solution is obtained by dissolving a polyimide precursor in an organic solvent, the polyimide precursor comprises:

A salt of a multifunctional amine represented b Formula (1):

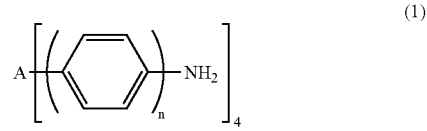

(wherein A represents a tetravalent organic group, and n represents an integer of 0 to 3) and tetracarboxylic diester represented by Formula (2):

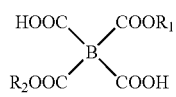

(2)

(wherein B represents a tetravalent organic group having 1 to 20 carbon atoms, and $R_1$ and $R_2$ each represent independently an alkyl group having 1 to 5 carbon atoms).

2. The polyimide thin film as described in claim 1, wherein A in Formula (1) is an adamantine skeleton.

3. The polyimide thin film as described in claim 1 comprising polyimide having a three-dimensional structure represented by Formula (3):

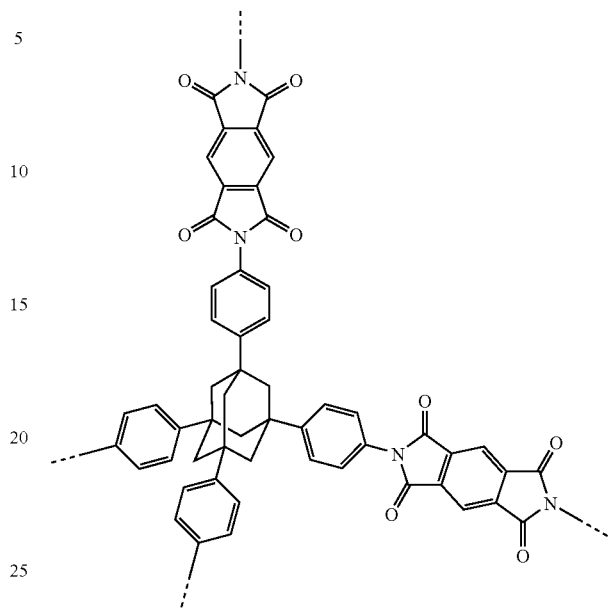

(3)

4. A layer insulating film using the polyimide thin film as described in claim 1.

5. A layer insulating film using the polyimide thin film as described in claim 2.

6. A layer insulating film using the polyimide thin film as described in claim 3.

* * * * *

UNITED STATES PATENT AND TRADEMARK OFFICE
CERTIFICATE OF CORRECTION

PATENT NO. : 7,087,311 B2
APPLICATION NO. : 11/207463
DATED : August 8, 2006
INVENTOR(S) : Takashi Kato et al.

It is certified that error appears in the above-identified patent and that said Letters Patent is hereby corrected as shown below:

On Title page

Please correct the Title (54) Delete "Polymer Compound, Precursor For The Same And Thin Film-Forming Method Using The Same Polymer Precursor" Insert --NOVEL POLYMER COMPOUND, PRECURSOR FOR THE SAME AND THIN FILM-FORMING METHOD USING THE SAME POLYMER PRECURSOR--

Signed and Sealed this

Sixth Day of March, 2007

JON W. DUDAS
*Director of the United States Patent and Trademark Office*